United States Patent [19]
Abraham et al.

[11] Patent Number: 4,887,995
[45] Date of Patent: Dec. 19, 1989

[54] METHOD OF TREATING SICKLE CELL ANEMIA

[75] Inventors: Donald J. Abraham, Murrysville, Pa.; Paul E. Kennedy, Lawrence, Kans.

[73] Assignee: University of Pittsburgh, Pittsburgh, Pa.

[21] Appl. No.: 693,629

[22] Filed: Jan. 22, 1985

[51] Int. Cl.$^4$ ............................................ A61M 37/00
[52] U.S. Cl. ........................................................ 604/4
[58] Field of Search ........................................ 604/4-6; 514/815, 108, 655, 649, 11, 222, 326

[56] References Cited

U.S. PATENT DOCUMENTS

| | | | |
|---|---|---|---|
| 3,255,241 | 6/1966 | Schultz et al. | 260/516 |
| 4,021,559 | 5/1977 | Gindicelli et al. | 514/815 |
| 4,022,893 | 5/1977 | Moyer | 514/655 |
| 4,048,325 | 9/1977 | Packer et al. | 514/815 |
| 4,060,630 | 11/1977 | Dolfini et al. | 514/815 |
| 4,137,309 | 1/1979 | Van Duzee | 514/108 |
| 4,261,980 | 4/1981 | Cort | 514/815 |
| 4,343,808 | 8/1982 | Broersma, Jr. et al. | 514/815 |
| 4,343,809 | 8/1982 | Broersma, Jr. et al. | 514/815 |
| 4,343,810 | 8/1982 | Broersman, Jr. et al. | 514/815 |
| 4,343,848 | 8/1982 | Broersma, Jr. et al. | 514/815 |
| 4,385,064 | 5/1983 | Pilley | 514/815 |
| 4,535,183 | 8/1985 | Kneen | 514/815 |

FOREIGN PATENT DOCUMENTS 0612755 1/1962 Belgium .

OTHER PUBLICATIONS

National Library of Medicine, "Sickle Cell Anemia", Special Literature Search, Jan. 1970–Jun. 1974.
National Library of Medicine, "Sickel Cell Anemia", Special Literature Search, Jul. 1974–Mar. 1978.
"Hemoglobin and the Sickling Cell" by Larry Varner, Pitt Capsule, pp. 4–18.
Cragoe et al., "Agents for the Treatment of Brain Injury. 1. (Aryloxy) Alkonoic Acids", J. Med. Chem. 1982; 25, 564.
Schultz et al., J. Med. Pharm. Chem. 5 660 (1962).

*Primary Examiner*—C. Fred Rosenbaum
*Attorney, Agent, or Firm*—Arnold B. Silverman

[57] ABSTRACT

A method of treating a person for sickle cell anemia including administering to the patient's blood a therapeutically effective dosage of ethacrynic acid. The dosage may be administered to blood removed from the patient which blood after addition of the compound is restored to the patient or by other means such as orally.

6 Claims, No Drawings

METHOD OF TREATING SICKLE CELL ANEMIA

BACKGROUND OF THE INVENTION

1. Field of the Invention

This invention relates to a method of treating sickle cell anemia and, more specifically, it relates to a method of resisting sickling of hemoglobin in a sickle cell anemia patient.

2. Description of the Prior Art

Sickle cell anemia is a hereditary blood disease which can afflict African, Mediterranean and Mideastern peoples. The anemia results from the physical aggregation of a mutant hemoglobin protein constituent in red blood cells. This aggregation results in a distortion in shape of deoxygenated red blood cells and causes impairment of flow of the blood through the capillaries (sickle cell "crises"). As the principal function of hemoglobin is to transport oxygen from the lungs to body tissues, efficient flow of oxygen throughout the body's tissues is impeded by the anemia due to a lower number of red blood cells. Sickle cell anemia also may have an indirect effect on the heart, lungs, kidneys, spleen, hips and brain. Sickle cell anemia crises can be extremely painful, can result in infections such as pneumonia, can result in skin ulceration, can contribute to strokes and seizures in the one afflicted and can also result in the development of chronic bone infections.

In general, the result of the differences between cells containing hemoglobin A, the normal hemoglobin, and hemoglobin S, the sickle cell hemoglobin, is that the former cell is generally flexible and bioconcave discoid in shape, while the latter is more rigid and crescent shaped and typically has pointed ends. This rigidity and distortion in shape causes the cells to be lodged in the capillary. Hemoglobin molecules contain two beta polypeptide chains and two alpha polypeptide chains. In the sickle cell hemoglobin, a mutation is present in the beta chains. More specifically, the sixth amino acid of each beta chain is changed from glutamic acid to valine. As a result of this mutation, hemoglobin S upon deoxygenation polymerizes and causes the cell to assume the elongated, sickle-like configuration. As the sickle cells have a much shorter life span than normal red cells, the effect on the body is to deplete the total volume of blood cells thereby creating an anemic condition.

Electrophoresis is one of the well established laboratory tests employed in diagnosing sickle cell anemia. Electrophoresis tests determine whether an individual has sickle cell anemia (homozygous) or merely the sickle cell trait (heterozygous). The latter refers to an individual not having the disease but having the capability of transmitting the disease to offspring if mated to anoter heterozygote. Treatment for the various complications which have resulted from sickle cell anemia are known and should be distinguished from prophylactic treatment generally (unknown) which would eliminate the occurrence of the complications and adverse symptoms. Currently, symptomatic treatment is available. For example, one can treat the symptoms by using analgesics for pain, and antibiotics for infection, but these approaches do not arrest the underlying sickling phenomena.

There remains, therefore, a very real and substantial need for a treatment method which minimizes the adverse consequences of sickle cell anemia by directly inhibiting the underlying cause of sickle cell crises.

SUMMARY OF THE INVENTION

The present invention has met the above-described need by providing a method which preferably involves administering to a person a therapeutically effective dosage of ethacrynic acid. This dosage is preferably administered by the acid being reacted extracorporeally with the patient's own blood or orally. In the former approach the acid is preferably administered to stored blood samples taken from patients and then readministered.

It is an object of the present invention to provide a method of treating a sickle cell anemia patient's blood so as to reduce undesired sickle cell crises.

It is another object of the present invention to provide an effective means for resisting undesired sickling of hemoglobin in sickle cell anemia patients.

These and other objects of the invention will be more fully understood from the following description of the invention.

DESCRIPTION OF THE PREFERRED EMBODIMENTS

In the preferred method of the present invention a sickle cell anemia patient is administered a therapeutically effective dosage of ethacrynic acid. This compound may be represented as follows:

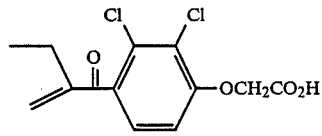

As this is a commercially available compound which has been marketed as a diuretic agent and for the treatment of certain brain injuries, those skilled in the art know how to prepare the compound and disclosure of the same is not required herein. See generally Schultz et al., J. Med. Pharm. Chem 5, 660 (1962); U.S. Pat. No. 3,255,241 and Belgian Patent 612,755. See also Cragoe et, J. of Med. Chem. 1982, 25, 567.

It is generally preferred to administer to a patient a dosage of less than about 100 mg./day with a preferred range being about 50 to 100 mg./day.

It will generally be preferred to administer the compound in a therapeutically effective dosage extracorporeally or orally. As the compound has known dieuretic effects it may be desirable to have the patient consume fluids administered orally in order to offset any fluid loss which may be experienced.

As the compound has known diuretic effects it is preferred to react it with blood removed intravenously from the patient. The reacted blood is washed thoroughly to remove the excess or nonpermanently bound drug and then the reacted blood is returned to the individual. This extra-corporeal approach may be performed by employing quantities of blood on the order of one pint per time.

EXAMPLE 1

An example of extracorporeal treatment will be considered.

One pint of homozygous blood cells removed from a patient are washed with a 1 to 3 mM. solution of the sodium salt of ethacrynic acid. This washing is performed until the Hemoglobin S is substantially completed converted to the new species having the ethacrynic acid bound to the Hemoglobin. This may be accomplished by washing the cells with about 4 to 6 l of 1 to 3 mM sodium salt of ethacrynic acid. The reaction is followed by electrophoresis which demonstrates the percentage of conversion to the new hemoglobin derivative. The reacted cells are then washed thoroughly with isotonic saline until substantially all of the excess and lightly bound drug is removed from the hemoglobin and the red cell membranes. The treated blood may then be reconstituted with plasma or nutrients or given as is to the patient.

In comparative tests which we reported in J. of Med. Chem., 1984, 27, 103–105, which is incorporated herein by reference, ethacrynic acid was compared with active agents (1) [(3,4-dichlorobenzyl)oxy]acetic acid (DiClBz$_2$) and (2) [(p-bromobenzyl)oxy]acetic acid (p-BrBz). The solubility assay measures the ability of a compound to increase solubility of sickle hemoglobin (HbS). At low concentrations (5 mM.) ethacrynic acid exhibited a higher solubility ratio than DiClBz and p-BrBz. The higher the ratio the higher the activity of the compound. Chromatographic separation confirmed the fact that desired tight covalent binding between the HbS and ethacrynic acid had occurred. Tests of transport across erythrocyte membranes confirmed the ability of ethacrynic acid to cross the red blood cell membrane and react with hemoglobin.

It is believed that the ethacrynic acid functions by convalently bonding to the hemoglobin at two locales and form a new kind of hemoglobin which does not sickle. This is not true of clofibric acid or other phenoxy acids.

In general it is preferred that the process be practiced extracorporeally although other means of administering the medication such as orally may be employed. The presently preferred dosage is about 50 to 100 mg./day.

It will be appreciated that the present invention provides a method for treatment of sickle cell anemia patients so as to resist undesired sickle cell anemia crisis. The method may advantageously be employed as a prophylactic.

Whereas particular embodiments of the invention have been described above for purposes of illustration, it will be evident to those skilled in the art that numerous variations of the details may be made without departing from the invention as defined in the appended claims.

We claim:

1. A method of treating a person for sickle cell anemia including administering to said person a therapeutically effective dosage of the compound ethacrynic acid by first withdrawing blood from said patient, introducing said compound into the blood and subsequently reintroducing said compound-bearing blood into said patient.

2. The method of claim 1 including administering said compound at a dosage rate of about 50 to 100 milligrams/day.

3. The method of claim 1 including administering said compound as a prophylactic means to resist a sickle cell crisis.

4. The method of claim 3 including and prior to reintroducing said blood into said patient washing said blood.

5. The method of claim 4 including establishing through the use of said ethacrynic acid a hemoglobin which has ethacrynic acid bonded thereto and which resists sickling.

6. The method of claim 4 including prior to reintroducing the blood into the patient reconstituting said blood.

* * * * *